United States Patent
Lam et al.

(10) Patent No.: US 12,090,512 B2
(45) Date of Patent: Sep. 17, 2024

(54) METHOD AND APPARATUS FOR PRE-TREATING A CATHETER

(71) Applicant: NOVA PLASMA LTD., Kibbutz Megiddo (IL)

(72) Inventors: Amnon Lam, Givat Oz (IL); Eliezer Fuchs, Megiddo (IL)

(73) Assignee: NOVA PLASMA LTD., Kibbutz Megiddo (IL)

( * ) Notice: Subject to any disclaimer, the term of this patent is extended or adjusted under 35 U.S.C. 154(b) by 958 days.

(21) Appl. No.: 16/980,045

(22) PCT Filed: Mar. 18, 2019

(86) PCT No.: PCT/IL2019/050298
§ 371 (c)(1),
(2) Date: Sep. 11, 2020

(87) PCT Pub. No.: WO2019/180703
PCT Pub. Date: Sep. 26, 2019

(65) Prior Publication Data
US 2021/0016318 A1    Jan. 21, 2021

(30) Foreign Application Priority Data

Mar. 18, 2018    (IL) .......................................... 258200

(51) Int. Cl.
*B05D 3/14* (2006.01)
*A61M 25/00* (2006.01)
(Continued)

(52) U.S. Cl.
CPC ........... *B05D 3/144* (2013.01); *A61M 25/002* (2013.01); *B05D 7/225* (2013.01);
(Continued)

(58) Field of Classification Search
CPC .... B05D 3/144; B05D 7/225; B05D 2254/06; A61M 25/002; H01J 37/32348;
(Continued)

(56) References Cited

U.S. PATENT DOCUMENTS

| | | |
|---|---|---|
| 9,192,040 B2 | 11/2015 | Ehlbeck et al. |
| 2010/0174245 A1 | 7/2010 | Halverson et al. |

(Continued)

FOREIGN PATENT DOCUMENTS

| | | |
|---|---|---|
| CN | 201020055 U | 2/2008 |
| CN | 103212096 A | 7/2013 |

(Continued)

OTHER PUBLICATIONS

International Search Report and Written Opinion from International Application No. PCT/IL2019/050298 mailed Jul. 7, 2019.

*Primary Examiner* — Xiuyu Tai
(74) *Attorney, Agent, or Firm* — Dorsey & Whitney LLP

(57) ABSTRACT

A method for pre-treating a catheter prior to using the catheter in a medical procedure, and a related apparatus, are provided. The method comprises exposing, in a plasma chamber positioned in a medical care center, and under sterile conditions, intraluminal surfaces and extraluminal surfaces of the catheter to plasma. The plasma is electromagnetically-generated adjacently to the intraluminal surfaces and extraluminal surfaces, thereby rendering, at least temporarily, the intraluminal surfaces and extraluminal surfaces of the catheter hydrophilic.

12 Claims, 3 Drawing Sheets

(51) Int. Cl.
*B05D 7/22* (2006.01)
*H01J 37/32* (2006.01)
*H05H 1/24* (2006.01)

(52) U.S. Cl.
CPC .. *H01J 37/32348* (2013.01); *H01J 37/32394* (2013.01); *H01J 37/32403* (2013.01); *H05H 1/2406* (2013.01); *B05D 2254/06* (2013.01)

(58) Field of Classification Search
CPC ........... H01J 37/32394; H01J 37/32403; H01J 37/32; H01J 37/32825; H01J 37/32733; H01J 37/32091; H01J 37/32715; H01J 37/321; H01J 37/32798; H01J 37/32568; H05H 1/2406; H05H 2245/30; H05H 2245/36; H05H 1/2425; H05H 2245/60; H05H 2245/32; H05H 1/2418; H05H 1/2465; H05H 1/466; G02B 27/0006; G02B 1/18; A61N 1/44; A61B 2018/147; A61B 1/253; A61B 1/127; A61L 2202/24; A61L 2/14; A61L 27/50; A61L 27/18; A61L 2300/406; A61L 2430/04; A61L 2400/18; C08L 83/04

See application file for complete search history.

(56) References Cited

U.S. PATENT DOCUMENTS

2016/0319433 A1\* 11/2016 Pavlinak ............... C23C 16/513
2017/0165029 A1   6/2017 Armour et al.
2020/0297881 A1\* 9/2020 Weltmann ............ H05H 1/2406

FOREIGN PATENT DOCUMENTS

| EP | 2174671 B1 | 4/2014 |
| EP | 2937102 B1 | 11/2017 |
| WO | 2009067682 A2 | 5/2009 |
| WO | 2012053083 A1 | 4/2012 |
| WO | WO 2017/042806 \* | 3/2017 |

\* cited by examiner

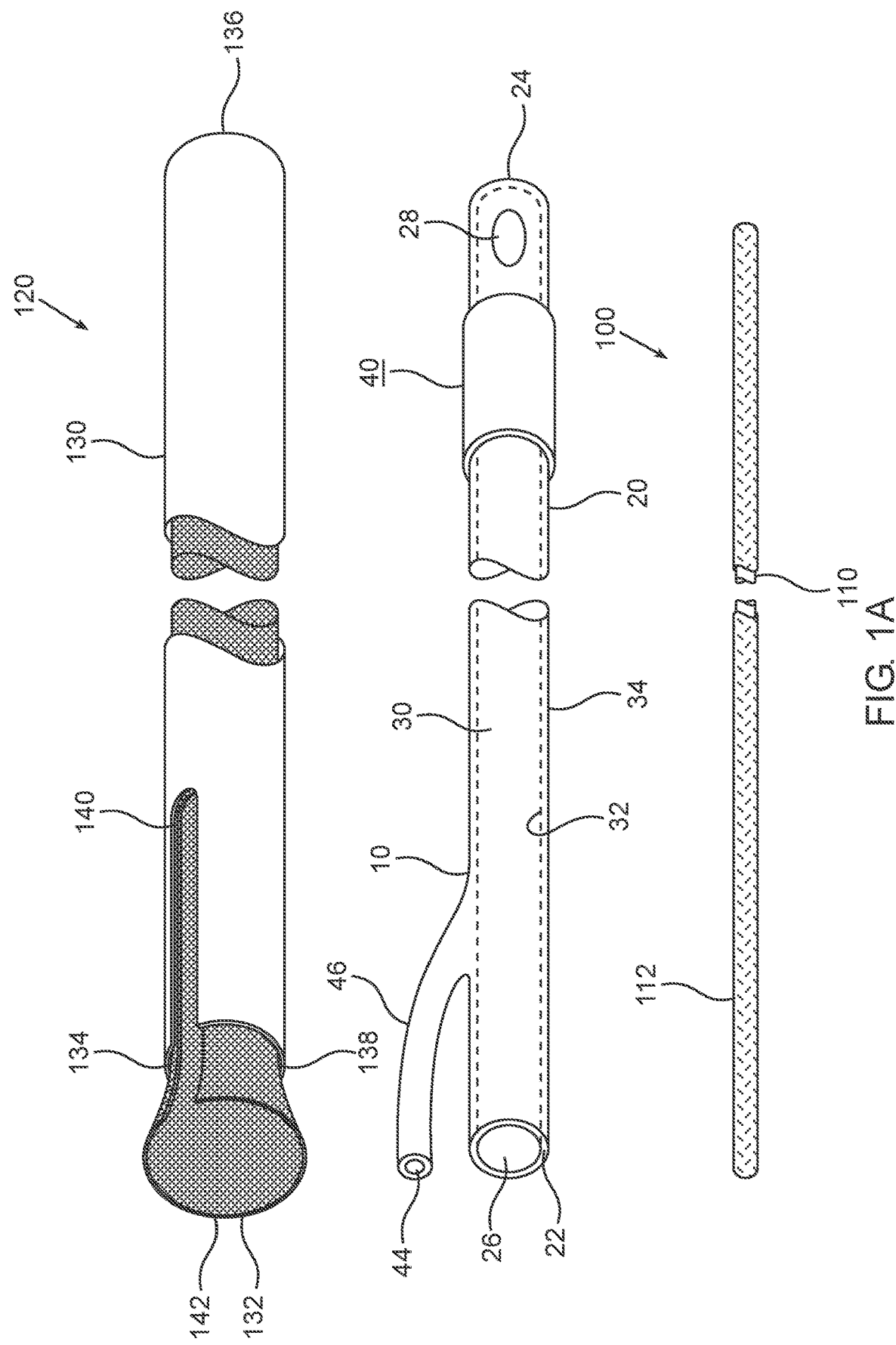

METHOD AND APPARATUS FOR PRE-TREATING A CATHETER

FIELD OF THE INVENTION

The invention, in some embodiments, relates to the field of pre-treating a catheter by exposing the catheter to physical plasma prior to using the catheter in a body of a live subject, and to related methods, devices and apparatuses.

BACKGROUND OF THE INVENTION

Plasma refers herein to ionized fluid, including positively charged ions and negatively charged electrons, wherein the whole volume of the ionized fluid is roughly neutral. Positively charged ions are generally referred to herein simply as "ions" whereas negatively charged electrons are referred to herein as "electrons". Neutral atoms and molecules are referred to as "neutrals". Non-thermal (or "cold") plasma refers to plasma wherein the neutrals' temperature, dictated by the neutrals' average random velocity, is low, e.g. below about 55 degrees C. or even below about 40 degrees C.

Plasma is known to affect surfaces of objects that are exposed to the plasma. More specifically, treating medical catheters by plasma for achieving one or more of several goals is known. For example, catheters may be plasma treated for sterilization. A typical process involves hydrogen peroxide solution injection into an evacuated sterilization chamber that houses the catheter, wherein the solution is evaporated. The hydrogen peroxide vapor diffuses through the chamber, exposing all surfaces of the catheter to the vapor, and initiates the inactivation of microorganisms. An electrical field created by a radio frequency electromagnetic (EM) field is applied to the chamber to create a gas plasma and generating microbicidal free radicals (e.g., hydroxyl and hydroperoxyl). The excess gas is then removed and the sterilization chamber is ventilated by filtered air. The by-products of the cycle (e.g., water vapor and oxygen) are nontoxic and eliminate the need for aeration. Thus, the sterilized materials can be handled safely, either for immediate use or for storage. A typical sterilization cycle by plasma takes a few tens of minutes, typically 30-70 min. The process is believed to inactivate microorganisms primarily by the combined use of hydrogen peroxide gas and the generation of free radicals (hydroxyl and hydroperoxyl free radicals) during the plasma phase of the cycle.

Treating catheters by plasma is also employed to facilitate adhesion of various coatings on the catheter's surfaces, typically in the catheter's manufacturing line. Generally, surfaces of objects exposed to plasma may often be affected so that some characteristics of the surface change following such exposure. It is believed that surface energy and chemistry may change due to the generation of reactive species in the plasma, and deposition of chemical substances on the surface. A featured result may be a modification of the surface properties, particularly surface energy. For example, plasma generated in a gaseous atmosphere comprising argon or helium with an admixture of oxygen, or even in air at low or at atmospheric pressure, may render the external surface of an object exposed to the plasma more hydrophilic.

Patent application publication number US20100174245 of Halverson et al. discloses a method and system for pre-treating the lumen of a polymer catheter or small diameter tubing. A vacuum chamber includes a microwave port and a microwave supply subsystem including a microwave generator. A circular polarizer produces circularly polarized microwaves propagated into the vacuum chamber via the port at a frequency which produces electron cyclotron resonance. A magnetic coil about the vacuum chamber generates a magnetic field in the vacuum chamber with magnetic field lines co-linear with the propagation direction of the microwaves. A catheter manifold positions at least one catheter in the vacuum chamber and supplies a gas within the catheter lumen to generate a plasma in the lumen for pre-treating the same.

Patent application publication number WO2009067682 of Roy et al. discloses a self sterilizing device, e.g. a catheter, capable of sterilizing a surface of the device using plasma fields. The self sterilizing device may include one or more first electrodes located proximate the surface; one or more second electrodes located proximate the one or more first electrodes, and a power source for applying a voltage across at least one of the one or more first electrodes and at least one of the one or more second electrodes so as to generate the plasma that sterilizes or decontaminates at least a portion of the surface. The one or more first electrodes may comprise a first wire electrode, the one or more second electrodes may comprise a second wire electrode, and the first wire electrode and the second wire electrode are braided. The surface may be an outer surface or an inner surface of the catheter, wherein the braided first wire electrode and second wire electrode are positioned within a body of the catheter.

In spite of tremendous efforts to maintain safe catheterization during medical procedures, catheterization-associated infections remain a major problem, especially in prolonged catheterizations, namely when a catheter is left in the subject's body for a long time. An exemplary field is urinary catheterization, where a catheter is inserted through the urinary tract of the patient to drain the bladder. Experience shows that in such cases, where a catheter is left in a patient's body as part of a routine medical treatment, Urinary Tract Infections (UTI) may often develop within days. Statistics show that among UTIs acquired in the hospital, approximately 75% are associated with a urinary catheter, whereas the risk of infection increases by about 5% with each additional day the catheter is installed.

There is an unmet need for increasing the safety of procedures involving catheterization by preventing or delaying the colonization of a catheter by bacteria.

SUMMARY OF THE INVENTION

According to some aspects of the present invention it has now been shown that activating by plasma a surface of a catheter, as is described in detail herein below, prevents, or at least considerably delays the attachment of bacteria onto the treated surface. The prevention effect is achieved particularly on polymer surfaces and also on metallic surfaces.

Current research identifies several stages in the process of bacteria proliferation on a catheter surface, eventually causing infection. At some point following catheterization, bacteria attach to the catheter surface. The first attachment of the bacteria is influenced by attractive or repelling forces that vary depending on various factors including nutrient levels, pH, and the temperature of the attachment site. In this stage, flagella and chemotaxis play an important role in avoiding the action of the hydrodynamic and repulsive forces as well as selecting the surface respectively. Thus, from a preventive point of view, bacteria attachment in this stage is the most vulnerable, and attachment prevention is the most likely.

After attachment, bacteria express adhesion proteins on their surface, which enforce the attachment, making the attachment what is termed as "irreversible". Then, bacteria rapidly multiply and colonize the surface of the device, producing a thick matrix known as a biofilm Once biofilm formation has taken place, bacteria within it are resilient to anti-microbial agents. In other words, bacteria within biofilms are often protected from the action of antibiotics. Infection of the urine and the bladder itself can then result through the intimate connection between the colonized catheter and the sterile bladder. Lastly, when biofilms are fully mature, detachment may occur. Detachment allows cells to again take on a planktonic state and thereby form biofilm in other sites. Thus, unless the colonized catheter is removed, the biofilm has the potential to re-seed initially-sterile sites, e.g. the bladder.

Focusing on the likelihood mentioned above of initial attachment of bacteria onto surfaces of a catheter, current research further acknowledges the importance of the presence of host cells on these surfaces. The term "the race for the surface" is used to describe the competition between host tissue cell integration and bacterial colonization on implants and catheters surfaces, whereas the fate of an implant or a catheter device in a subject's body is dictated by the outcome of the "race". It is assumed that host cells may "defend" the device surface from invading pathogens by various mechanisms including integration and vigorous immune competence, which is particularly effective only at the initial stage of bacteria colonization (namely the stage of initial attachment). If, in contrast, bacteria colonization matures to form a biofilm as described above, it is the bacteria that become protected from the host body immune mechanisms, as well as from antibiotics provided externally.

There is thus provided a method for pre-treating a catheter prior to using the catheter in a medical procedure. The method is aimed at elevating the likelihood of the medical procedure's safety and efficacy, specifically at preventing the initial attachment of bacteria onto the catheter, and for that end the method is preferably carried out immediately or soon before the medical procedure to maximize the method's effectiveness.

The method comprises exposing, in a plasma chamber and under sterile conditions, intraluminal surfaces and extraluminal surfaces of the catheter to plasma, the plasma being electromagnetically-generated adjacently to the intraluminal and extraluminal surfaces. Such exposure sets, at least temporarily, a surface characteristic of the said surfaces. According to some embodiments the surface characteristic is hydrophilicity and the setting sets the surfaces hydrophilic. The inventors have found that activating by plasma a surface of a catheter, as is described in detail herein below, prevents, or at least considerably delays the attachment of bacteria onto the treated surface. The prevention effect is achieved particularly on polymer surfaces and also on metallic surfaces.

It is emphasized that the method is not aimed at sterilizing surfaces of the catheter, but rather generating a physico-chemical effect on the surface, and may thus benefit a catheter which is already sterilized. Without being bound to a particular theory or hypothesis, the inventors believe that a suitable plasma treatment may enhance or increase the surface energy of the treated surface, thereby increasing the surface wettability by a polar liquid such as water, an aqueous solution or blood. Such plasma treatment is thus believed to enhance initial attachment of various components of the innate immune system to the treated surface, and thereby gain advantage in the "race for the surface" over infectious bacteria.

After the plasma treatment and before the medical procedure, portions of the intraluminal surfaces and extraluminal surfaces may further be coated by exposing the said surface portions to a liquid, gel or powder. According to some embodiments the catheter may thus be coated, for example, with a bioactive material or by a coating that includes a bioactive agent. According to some embodiment the catheter may thus be coated, for example, with an antibiotics agent. Such coating may in some embodiments comprise for example immersing the catheter in a bath of antibiotic liquid so that the antibiotic liquid wets the plasma-treated surfaces of the catheter, in a process that takes a few seconds or a few tens of seconds at most. In some embodiments such coating may comprise a more enhanced process that may include for example drying or otherwise stabilizing the coating material on the surfaces of the catheter. In any case, however, such optional coating is performed under sterile conditions and just prior the use of the catheter in the medical procedure.

The method thereby provides for use in the medical procedure a catheter having hydrophilic intraluminal and extraluminal surfaces following being treated by plasma, and, optionally, further being coated. The plasma treatment prevents or at least considerably delays bacteria colonization on the treated surfaces, possibly by facilitation, enhancement and acceleration of host body cells availability to these surfaces. Yet further prevention or delay of bacteria colonization may be achieved by a suitable coating. The plasma treatment may enhance adhesion of a coating material to which the treated surfaces may be exposed. For example, the plasma treatment may render the treated surfaces hydrophilic, thus facilitating and enhancing wetting—possibly complete wetting—by a polar liquid such as water or an aqueous solution or an aqueous suspension. Such wetting or complete wetting may thus provide an effective coating of the surfaces with a bioactive agent included in the liquid used.

The method described herein is intended to be carried out shortly before the medical procedure, and preferably immediately before the medical procedure, for two reasons. First, it is noted that the beneficial effects of exposure to plasma of the catheter's surfaces are often temporary, and demonstrated improved or enhanced hydrophilicity, decreases as the time interval between exposure of the catheter to plasma and installing the catheter in a body, increases. In other words, the shorter the time between the plasma treatment and the insertion of the catheter to the patient's body, the more effective the plasma treatment is, in terms of higher hydrophilicity and in terms of decreased bacteria colonization.

Second, the plasma treatment according to the teachings herein should not, preferably, be followed by a sterilization process, because such a sterilization process would likely impair or ruin the effects of the plasma treatment. It should further be appreciated that the likelihood of attachment of infectious bacteria onto the catheter's surfaces is believed to be lower, as the time of exposure to room atmosphere (even if nominally sterile) of the catheter before installment, is shorter. Hence the catheter should preferably be sterile prior to the plasma treatment, and the plasma treatment should preferably be made under sterile conditions, so that the catheter is maintained sterile. Consequently, the time period between the plasma treatment and the catheter installation should be minimized, as described above.

It is thus generally required that the plasma treatment would be performed within two days prior to the installment of the catheter in the patient's body, and more preferably within the same day of the installment procedure. Still more preferably, the plasma treatment should be performed less than 6 hours or less than 1 hour prior to the installment. Yet more preferably the plasma treatment should be carried out less than 30 minutes or less than 20 minutes or even less than 10 minutes prior to the installment.

Characteristics of the electric field that could generate plasma in a fluid, may depend strongly on characteristics of the fluid itself, in addition to the geometry involved (such as shape and configuration of electrodes used for the application of the electric filed, distance between the electrodes etc.). Generally, if the fluid is a gas, the higher the pressure of the gas, the higher the electric field should be to ignite plasma. Also, some gases ignite at lower fields than others. For example, helium gas at atmospheric pressure will ignite at an RF field (e.g. in a frequency between 1 MHz and 15 MHz) of about 7 kV over a distance of 1 cm between electrodes, and at a voltage of about 200 V in 0.8 kPa. With a similar configuration of electrodes and at similar field frequencies, air will ignite at a voltage of about 20 kV in atmospheric pressure and at a voltage of about 800 V in 0.8 kPa. Thus, according to some embodiments plasma is excited according to the teachings herein in diluted air, that is to say in a vacuum chamber or a sealed tube from which air was pumped out to reach a pressure of less than about 0.01 Atm, or even less that about 0.1 Atm. According to some embodiments the plasma treatment is provided at ambient conditions namely in air at room pressure. According to some embodiments plasma treatment is provided in air at atmospheric pressure, albeit with an admixture of an additional gas such as argon or helium, to facilitate plasma ignition. According to some further embodiments, plasma treatment may be provided in an atmosphere containing a mixture of air and argon, or another mixture containing one or more inert gases (e.g. helium or nitrogen, to name a few) and oxygen, at a low pressure. Low pressure herein means lower than 1 Atm., e.g. below about 0.1 Atm or below about 0.01 Atm.

Certain embodiments of the present invention may include some, all, or none of the above advantages. Further advantages may be readily apparent to those skilled in the art from the figures, descriptions, and claims included herein. Aspects and embodiments of the invention are further described in the specification hereinbelow and in the appended claims.

Unless otherwise defined, all technical and scientific terms used herein have the same meaning as commonly understood by one of ordinary skill in the art to which this invention pertains. In case of conflict, the patent specification, including definitions, governs. As used herein, the indefinite articles "a" and "an" mean "at least one" or "one or more" unless the context clearly dictates otherwise.

BRIEF DESCRIPTION OF THE FIGURES

Some embodiments of the invention are described herein with reference to the accompanying figures. The description, together with the figures, makes apparent to a person having ordinary skill in the art how some embodiments of the invention may be practiced. The figures are for the purpose of illustrative discussion and no attempt is made to show structural details of an embodiment in more detail than is necessary for a fundamental understanding of the invention. For the sake of clarity, some objects depicted in the figures are not to scale.

In the Figures.

DETAILED DESCRIPTION OF SOME EMBODIMENTS

Figure 1B:
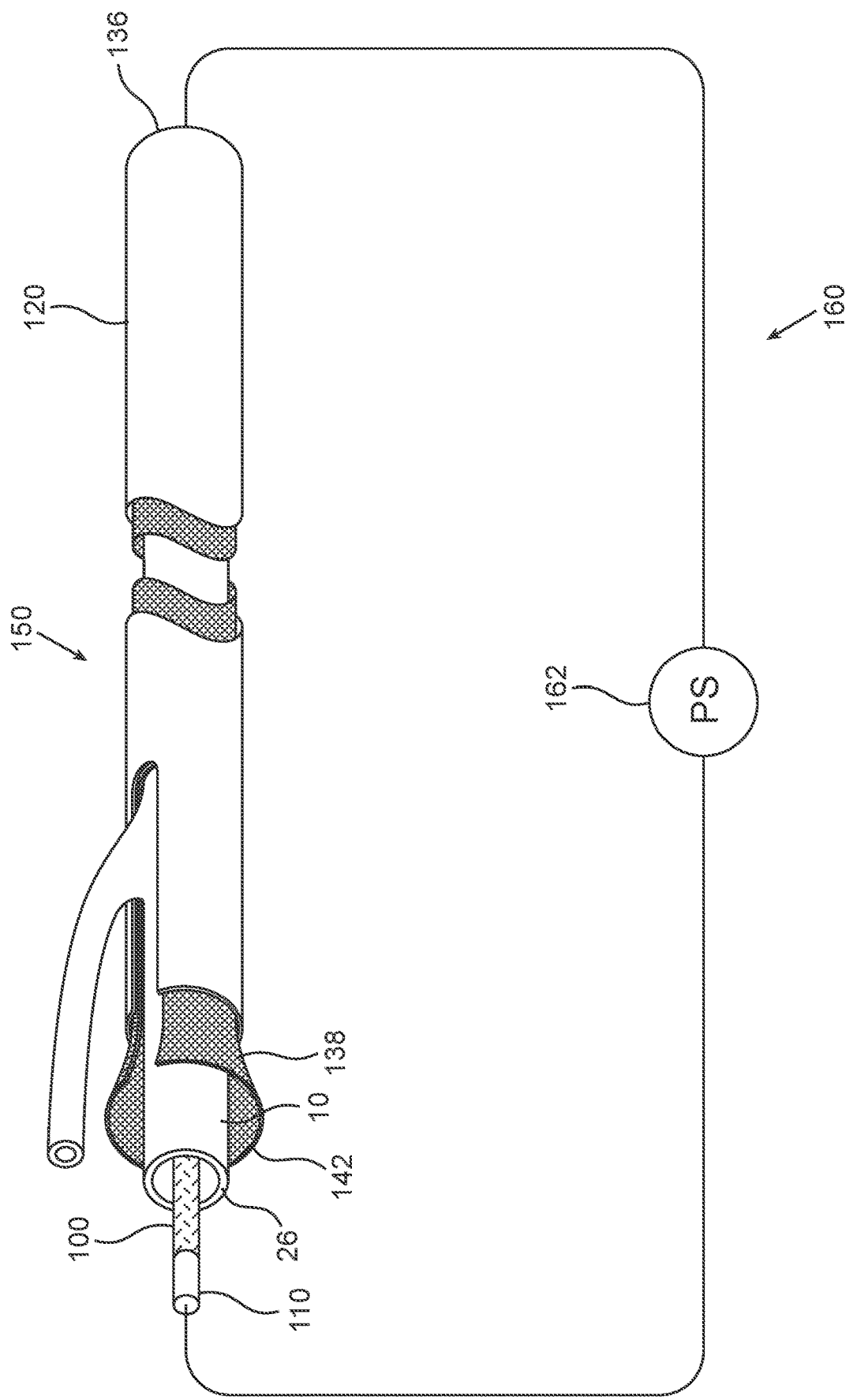
FIG. 1A schematically depicts a urinary catheter as is known in the art, and an embodiment of an internal electrode and an external electrode configured to enable plasma generation adjacent intraluminal and extraluminal surfaces of the catheter, FIG. 1B schematically depicts a device comprising the internal electrode and external electrode of FIG. 1A, arranged in an electric circuit, for use, and FIG. 2 schematically depicts an embodiment of a plasma chamber suitable for plasma treating the catheter of FIG. 1A according to the teachings here.

The principles, uses and implementations of the teachings herein may be better understood with reference to the accompanying description and figures. Upon perusal of the description and figures present herein, one skilled in the art is able to implement the teachings herein without undue effort or experimentation. The specific embodiments described herein below are concerned with a urinary catheter as a non-limiting example. It should nevertheless be understood that the principles of the teachings herein are not limited to any particular type of catheters and may be employed, mutatis mutandis, to any catheter having a tube portion with an internal lumen and an opening allowing insertion of an internal electrode into the lumen.

FIG. 1 schematically depicts in a simplistic drawing a urinary catheter 10 as is known in the art. Urinary catheter 10 is intended to be inserted into a urinary tract of a human patient, e.g. to allow drainage of the patient's bladder.

Urinary catheter 10 comprises an elongated flexible tube 20 extending between a proximal end 22 and a distal end 24, and defining an elongated lumen 30 by an intraluminal surface 32 thereof. Flexible tube 20 further comprises a proximal opening 26 on proximal end 22, a distal opening 28 near or at distal end 24 and an extraluminal surface 34 along the external surface of flexible tube 20. Elongated lumen 30 provides fluid communication between proximal opening 26 and distal opening 28, so that a fluid may enter flexible tube 20 through one of proximal opening 26 and distal opening 28, flow through lumen 30 and exit flexible tube 20 through the other of proximal opening 26 and distal opening 28.

Urinary catheter 10 further comprises an inflatable balloon 40, having a deflated relaxed state, disposed around flexible tube 20 near distal end 24. An inflating lumen, not explicitly depicted here, extends between an inflating lumen proximal opening 44, positioned on an inflating tube branch 46 of catheter 10, and an inflating lumen distal opening (not shown here) located inside inflatable balloon 40. The inflating lumen thus provides fluid communication between the inner volume of inflatable balloon 40 and inflating lumen proximal opening 44. By pressurizing a fluid such as gas or liquid into inflatable balloon 40 through the inflating lumen, inflatable balloon 40 may be inflated from its relaxed state to an inflated state. When catheter 10 is installed in a patient's urethra, inflatable balloon 40 is typically situated inside the bladder, and, when inflated, stabilizes the catheter in place, namely prevents the catheter from sliding outside the urethra. In a typical use, urinary catheter 10 may be installed in a patient's urethra for a short or a long period of time, ranging from several hours to days, to weeks and even months.

FIG. 1 further depicts schematically an internal electrode 100 and an external electrode 120, configured to establish a plasma-generating electromagnetic field, as is further detailed below, when being supplied with a suitable electromagnetic power. Internal electrode 100 comprises an elongated conductor 110, enveloped with a spacer net 112. Internal electrode 100 is dimensioned and configured to be inserted into elongated lumen 30 of urinary catheter 10. Elongated conductor 110 may be made of metal, and is tough enough so as not to fold or crumple during insertion into elongated lumen 30. According to some embodiments elongated conductor may be flexible, so as to be able to follow a curved route dictated by the internal lumen 30 during insertion. Elongated conductor 110 may be made as an elongated wire of a flexible metal, e.g. spring steel. Additionally or alternatively, elongated conductor 110 may be formed as a coil spring, for example as a fully depressed coil spring (like a tension spring) for exploiting flexibility and facilitating the insertion. The insertion may be carried out in the clinic prior to activating plasma; or in the catheter manufacturing site or immediately after a sterilization process, prior to storing the catheter, as is further detailed and explained below. External electrode 120 comprises a conductor sleeve 130 enveloping an external spacer net 132. Conductor sleeve 130 may be made of an electric conductor, e.g. metal. Conductor sleeve 130 may be shaped as an elongated tube extending between an electrode proximal end 134 and an electrode distal end 136. Conductor sleeve 130 has an electrode opening 138 on electrode proximal end 134, for insertion of catheter 10 (distal end 24 first) thereto. On electrode distal end 136, conductor sleeve 130 is preferably sealed. Conductor sleeve 130 optionally comprises a slot 140 stretching from electrode opening 138 along a portion of conductor sleeve 130 for enabling the inflating tube branch 46 to remain outside the external electrode when catheter 10 is inserted into the external electrode. It is noted that conductor sleeve 130 may have shapes and geometries different from the one described in FIG. 1. Generally, conductor sleeve 130 that at least partially envelops the catheter along the catheter's length, may function suitably well as a conducting member of external electrode 120. Accordingly, conductor sleeve 130 may be shaped as a helical coil (not necessarily fully depressed) or a perforated tube, or a wired net in the form of a closed tube, similar in shape to external spacer net 132, just to name a few examples. Conductor sleeve 130 may in some embodiments be rigid, and in some embodiments may be flexible, to allow easy insertion of a curved catheter thereto.

Spacer net 112 is configured to maintain a space gap between conductor 110 and intraluminal surface 32, so that two conditions are met: (a) a minimum distance gap between conductor 110 and intraluminal surface 32 (as may be approximated for example by the thickness of the spacer net) is maintained, that suffices for ionization of the fluid (liquid or gas) in the space gap, when a plasma-generating EM field is applied. Specifically, elongated conductor 110 does not contact directly intraluminal surface 32. And (b) the accumulated area of spacer net 112 is as small as possible, so that spacer net 112 covers as little surface as possible of intraluminal surface 32 to allow as large a portion of the intraluminal surface 32 to be treated.

The desired distance gap between the conductor and the intraluminal surface is dependent primarily on the Mean Free Path (MFP) of charge carriers in the fluid, typically being free electrons, and on the applied field which should be high enough to allow such charge carriers to gain enough kinetic energy along the MFP to initiate ionization during a collision with a neutral molecule. At a pressure bellow 0.01 Atm (10 mbar), and a distance between electrodes of about 5 mm, effective plasma may be generated adjacently to the intraluminal and extraluminal surfaces of the catheter using the electrodes of FIG. 1 at an RF field generated by a 5 KV voltage at about 100 KHz. Plasma may further be generated with a similar configuration of electrodes and similar electrical field in an admixture of air and helium at a pressure higher than 0.1 Atm, and even at atmospheric pressure. It is further noted that when treating a catheter with a narrow lumen, a thin inner electrode 100 should preferably be used, with the benefit that a thin inner electrode generates a higher field (compared to a thick electrode) at a same voltage. In other words, the small distances between the intraluminal surface and the electrode resulting from the small diameter of the catheter, may be overcome by the use of an inner electrode thin enough to penetrate into the small-diameter lumen.

The typical size of holes in spacer net 112 is configured to ensure no contact between conductor 110 and intraluminal surface 32 along a single hole. At a spacer net thickness of 0.1 mm and possible curvature of tube 20, typical holes size may be below 10 mm, for example about 5 mm. It should be noted that According to some embodiments, suitable plasma may be generated according to the teachings herein without the use of spacer net 112 and/or external spacer net 132. According to some embodiments, internal electrode 110 and external electrode 120 may be entirely coated with an insulating layer such as an insulating lacquer to prevent direct contact of the catheter with the conductors of the electrodes. In such embodiments plasma may still be generated in the vicinity of the catheter surfaces, possibly except of points or regions where direct contact is formed between the coated electrode and the catheter. According to some embodiments even uncoated, exposed conductors may be used as electrodes. In such embodiments a risk of injuring the catheter surfaces at points or regions where the conductors contact the surfaces, may be larger.

For an 8 Fr urinary catheter for example, having a length of 280 mm, an outer diameter of 2.4 mm and an internal diameter of 1.7 mm, internal electrode 100 may thus have a total thickness of about 1.4 mm, with elongated conductor 110 made of a spring steel wire of 1.0 mm diameter, enveloped by spacer net 112 having a thickness of 0.1 mm Spacer net 112 may be made from an electric isolating polymer material such as nylon, Teflon, silicone, polycarbonate to name a few examples. Spacer net 112 may be formed in one of various shapes and forms, for example in a form of a wire net with wires having a thickness of 0.1 mm, spaced apart by 5 mm. Such spacer net might shade the intraluminal surface 32 along a surface portion smaller than about (0.1*2)/5=4%, hence plasma coverage of the intraluminal surface 32 in this example is therefore higher than 96%.

External spacer net 132 is configured to maintain a space gap between conductor sleeve 130 and extraluminal surface 34. External spacer net 132 is thus configured as a sock, having a net opening 142 on one end near electrode opening 138, and a blind end (not depicted here) near electrode distal end 136. Analogously to spacer net 112, external spacer net 132 is configured to prevent direct contact between conductor sleeve 130 and extraluminal surface 34, and to maintain a minimum distance gap therebetween for allowing plasma ignition in the gap as detailed and described above. Accordingly, external spacer net 132 may be formed similarly to spacer net 112, having for example a thickness of about 0.1 mm and holes of about 5 mm.

FIG. 1B schematically depicts a device 150 comprising internal electrode 100 and external electrode 120, arranged in an electric circuit 160, for use. Internal electrode 100 may be inserted into lumen 30 of catheter 10, preferably via proximal opening 26, substantially until the electrode reaches the distal end of the catheter from within the lumen. Likewise, catheter 10 with internal electrode 100 within, may be inserted into external electrode 120 via electrode opening 138 and net opening 142, until the distal end of the catheter reaches electrode distal end 136. Internal electrode 100 and external electrode 120 may be electrically connected to an EM power source 162, so that the power supplied by the power source generates an EM field between the electrodes. As is detailed further below, power source 162 is preferably an AC source, but additionally or alternatively may be, in some embodiments, a DC source. When the power source is activated, a plasma-generating EM field is established between the electrodes and the extraluminal and intraluminal surfaces of the catheter and consequently plasma is generated adjacently to said surfaces.

Figure 2:
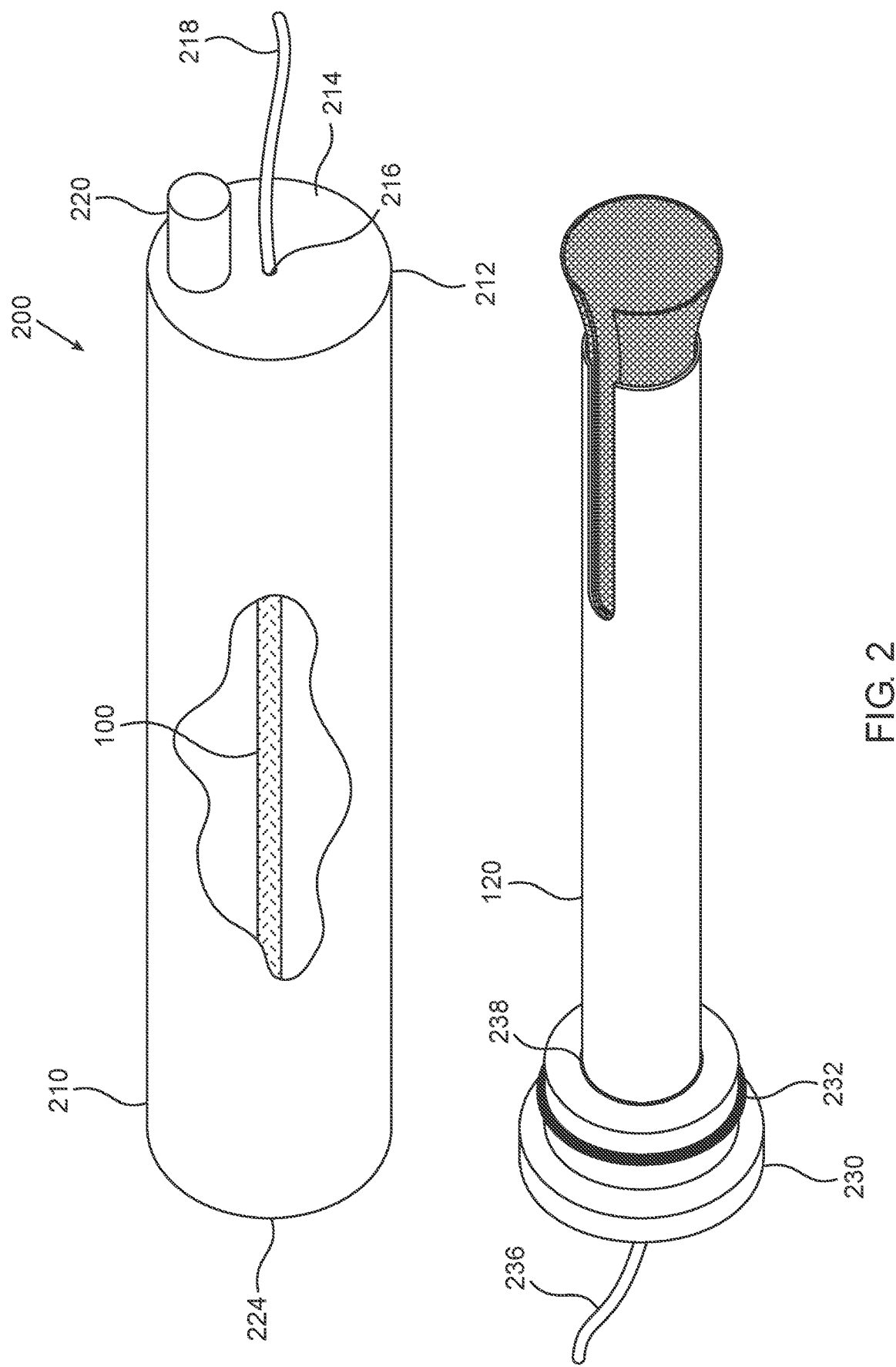

According to some embodiments, catheter 10 may be plasma-treated within a plasma chamber, in vacuum. FIG. 2 schematically depicts an embodiment of a plasma chamber 200 suitable for plasma treating catheter 10 according to the teachings here. Plasma chamber 200 comprises a hollow tube 210 sealed on one end 212 thereof by a flange 214. Plasma chamber 200 comprises internal electrode 100 electrically connected via a high voltage sealed feed through 216 in flange 214 to an internal electrode lead 218, configured to deliver high voltage electric signal to internal electrode 100. Plasma chamber 200 further comprises a gas port 220 fluidly connected, possibly via a valve (not depicted here) to the inside of hollow tube 210, and configured to enable pumping plasma chamber 200 by a vacuum pump (not shown here) and/or flushing plasma chamber 200 with a gas, e.g. helium or argon or nitrogen. Plasma chamber 200 further comprises a cover 230 having a seal 232 such as, for example, an O-ring, the cover being configured to close and seal plasma chamber 200 on an opening 224 thereof when closed. Cover 230 comprises external electrode 120 electrically associated with an external cathode lead 236 via an external cathode feedthrough 238, for delivering high voltage electric signal to external electrode 200.

For use, catheter 10 may be suitably positioned inside external electrode 120 on cover 230. The cover with the catheter installed may then be advanced towards hollow tube 210 so that internal electrode 100 is inserted into proximal opening 26 as described above. Cover 230 may be further advanced until hollow tube 210 is closed and sealed by cover 230. When plasma chamber 200 is sealed, the chamber may be pumped—evacuated—until a desired vacuum level is achieved inside the chamber, wherein plasma treatment may begin. For initiating plasma treatment when the required vacuum level is attained, high voltage, possibly at RF frequency, may be delivered to leads 236 and 218, thereby igniting plasma inside the plasma chamber and in the vicinity of the extraluminal and intraluminal surfaces of the catheter.

According to some preferred embodiments the EM field may be an AC field, possibly at RF frequencies. According to some embodiments EM field at a frequency between 10 KHz and 100 MHz may be selected. According to some embodiments the plasma generating field may be an RF field modulated by a low frequency AM signal. For example, a pulse modulation at a frequency between 10 Hz and 10 KHz and a duty cycle between 1% and 90% or even 95% may be used. It is noted that pulse modulation and duty cycle control may be a preferred method of managing the average power delivered to the plasma, because average power has a complicated dependency on other parameters of the EM field (e.g. voltage or frequency) but it varies linearly with the duty cycle.

It is further noted that using electrodes 100 and 120 according to the embodiments described above, plasma may be generated in a Dielectric Barrier Discharge (DBD) mode. In DBD mode of operation, the field-generating electrodes are separated by at least one dielectric layer that is disposed so as to interrupt any possible line of sight between the two electrodes or portions thereof. In the embodiments described above, at least the catheter itself functions as a dielectric that separates between the two electrodes, and hence prevents or at least significantly decays the occurrence of an arc between the electrodes. The catheter may therefore be considered as part of the electric circuit that generates the plasma, because the catheter's presence and its electrical and mechanical characteristics affect the operating parameters. For example, the presence of the catheter in between the electrodes generally necessitates a higher voltage (compared to a similar situation, devoid of the catheter) to initiate and maintain plasma generation. Yet, dielectric breakdown of the ionized fluid, accompanied by an arc, is usually prevented even at much higher voltages (compared to a similar situation, devoid of the catheter). Thus, although the presence of a catheter between the electrodes requires a relatively high voltage for plasma ignition, the catheter also ensures a relatively large range of voltages over which stable glow discharge occurs (adjacently to both surfaces of the catheter), with no risk of dielectric breakdown.

It is further noted that plasma generation involves various types of excitations, these excitations having various time constants for decay. For example, positively charged ions and negative charge electrons, generated by the excitation and ionization of initially neutral atoms and molecules, may recombine over a time scale shorter than a millisecond, e.g. on the order of magnitude of microseconds. Recombination of electrons and ions typically involves emission of light, such light is therefore emitted only over time scales equivalent to that of the recombination process.

Plasma may generally include also excited species which decay over times longer than recombination decay time, e.g. on the order of magnitude of 1 second, such as some types of free radicals. Thus, when plasma is generated at a distance from a zone to be treated and then guided towards that zone, only excited species that decay over relatively long times may survive the travel and affect the treated zone. Species with decay times shorter than the travel time from the plasma generation region to the treatment zone may decay during the travel, and consequently may not contribute to treatment.

It is therefore concluded that the generation of plasma as described herein, namely wherein the treated catheter surfaces are between the EM field generating electrodes, has a double-fold effect on the treated surfaces. Plasma is generated in the vicinity—preferably the immediate vicinity—of the treated surfaces, and while the treated surfaces are exposed to the excited species, including charged ions and electrons, generated by the EM field, the catheter material itself is subject to the strong plasma-generating field which affects a polarizing force across the catheter's walls. It is believed that this double-fold effect greatly enhances the surface excitation imposed on the catheter. It may be added that adequate plasma generation may be typically ascertained by a typical glow in the relevant regions and is directly responsible to obtaining the outcome of modifying the treated surfaces according to the teachings herein.

Particularly, according to some embodiments, such specific plasma excitation may render the treated surfaces perfectly wettable. Perfectly wettable herein means effecting a zero contact angle with a drop of water, which is equivalent to having a surface tension equivalent to or higher than that of water namely $$72 \cdot 10^{-3} \frac{N}{m}.$$

The inventors have further found that in some cases, a long stay of an untreated catheter in an aqueous environs may lead to gradual accumulation of bubbles on the catheter's surfaces. It is accordingly speculated that in a catheter deployed in a body of a patient, such bubbles, such isles of gas attached to the catheter, might, under suitable conditions, accommodate the preliminary settlement of bacteria more easily than regions of the catheter's surface which are in intimate, continuous contact with body fluids. Consequently, the formation of such bubbles might, under some conditions, facilitate and expedite the occurrence of an infection.

The inventors have found that an effective plasma treatment according to the teachings herein prevents or at least significantly slows down such accumulation of bubbles. The inventors have further found that plasma treatment that renders the catheter's surfaces highly wettable or even perfectly wettable, does not necessarily ensure the prevention of accumulation of bubbles when the catheter is submerged in water or in an aqueous solution. In other words, a plasma treatment that succeeds in prevention of accumulation of bubbles as described above, seems to be generating surface activation which is even higher than the surface activation that is necessary for perfect wetting. There is thus provided a method of pre-treating the catheter prior to using the catheter in a medical procedure. The method comprises applying a plasma-generating EM field in the vicinity of the surfaces, thereby exposing portions of the internal and external surfaces of the catheter to plasma, thereby activating the said portions of the surfaces. According to some embodiments, the surface activation effects a surface tension of the treated catheter surfaces which is higher than $$72 \cdot 10^{-3} \frac{N}{m}.$$

According to some embodiments, the surface tension of the treated portions is high enough to effectively prevent or at least noticeably reduce the attachment of gas bubbles to the treated surface portions, when the catheters is submerged in water or in an aqueous solution.

According to some embodiments, the catheter is plasma treated as described above soon before the medical procedure which employs the catheter. It is believed that, due to the temporary nature of the surface modification by plasma, the shorter the time gap between the plasma treatment and the deployment of the catheter in the subject's body, the more effective some types of modification will be. Also, the shorter the time gap is, the less likely it will be that the catheter is infected during the time gap.

There is therefore provided a method for pre-treating the catheter prior to using the catheter in a medical procedure, preferably soon before the medical procedure, preferably at the site where the medical procedure is carried out. It is most preferable that the plasma treatment according to the teachings herein is employed substantially immediately before the deployment of the catheter in the subject's body.

To minimize the time gap before the plasma treatment and the deployment of the catheter, the catheter is treated according to the teachings herein under sterile conditions. Thus, according to some embodiments, the catheter is provided sterile for the plasma treatment, and may be available for the medical procedure immediately after the method according to the teachings herein is fully carried out. It should be understood that performing the plasma treatment (or any other step of the method) in non-sterile conditions implies a further necessary step of sterilizing the treated catheter after the plasma treatment (and before the medical procedure). Such a step would be potentially detrimental to the modification of the treated surfaces of the catheter—because of the time gap necessary for sterilization, and also because the process of sterilization may chemically or physically affect such modification—and hence void or reduce the benefits of the method. It is emphasized that a sterilization step carried out after the plasma treatment may be detrimental to the surface modification according to the teachings herein, even if the sterilization procedure includes or constitutes of plasma sterilization. This is because plasma sterilization is itself a relatively lengthy procedure as discussed above, and also because plasma treatment intended to sterilize does not in itself provide the surface modification required according to the current invention and may thus deteriorate such surface modifications after they have been established.

Thus, according to some embodiments the method is carried out in a "closed system" approach. According to such embodiments, the catheter is supplied for the medical procedure in a sealed encasing which includes also the internal electrode 100 and the external electrode 120. In the sealed encasing the catheter and the electrodes are associated together as described above, namely the internal electrode is inserted into lumen 30 of the catheter and the catheter is inserted into the external electrode. Each of the electrodes is electrically associated with an electric conductor, e.g. an electric wire, which extends out of the sealed encasing to form an electric contact. According to some embodiments the electrodes may additionally or alternatively be electrically associated with electrical contacts outside the sealed encasing, without having a direct Galvanic contact with such electrical contacts. According to some such embodiments the electrodes may be for example capacitively coupled with the electrical contacts outside the sealed encasing.

The sealed encasing may be filled with a gas of a predefined composition such as filtered air or another gas, e.g. an inert gas (for example, argon or helium or nitrogen or a combination thereof or another inert gas), at atmospheric pressure, or alternatively with air or inert gas at low pressure, e.g. below about 0.5 Atm, or below about 0.2 Atm or below about 0.1 Atm or below about 0.01 Atm. The sealed encasing may be configured to be sealed so as to maintain the composition of the gas there inside unchanged during a projected storage period and/or shipment period, so that plasma activation is eventually done in the pre-defined gas composition with which the sealed encasing was filled.

Generating plasma adjacently to the intraluminal and extraluminal surfaces of the catheter as described herein may thus be accomplished by connecting or otherwise electrically associating the internal and external electrodes to a plasma generating power source via the electric contacts of the sealed encasing. Plasma is then generated inside the sealed encasing, following which the sealed encasing may be opened under sterile conditions and the catheter may be removed from the sealed encasing, detached from the electrodes and taken for the medical procedure.

It is noted that a suitable plasma treatment according to the teachings herein may take as little as less than 10 minutes, preferably less than 5 minutes, yet preferably less than 2 minutes, and most preferably even less than 1 minute.

According to some additional or alternative embodiments, the method is carried out in an "open system" approach. According to such embodiments, the catheter is supplied for the medical procedure under sterile conditions in a sealed package. The package may then be opened in a sterile field, and the catheter is then taken for a plasma treatment according to the description above. The plasma treatment may be carried out in a plasma chamber situated in the surgery room or in close vicinity to the location where the medical procedure is intended to be carried out. The plasma chamber may include therein the internal electrode and the external electrode, which may be associated with the catheter as described above, for plasma activation. The plasma chamber may be closed and sealed and according to some embodiments may be evacuated from air, and/or filled with a different gas, e.g. an inert gas, e.g. argon or helium. Plasma generation may then be employed by activating a power source electrically connected or otherwise electrically associated with the internal and external electrodes. It should be understood that the interior of the plasma chamber is maintained sterile so that plasma treatment is provided to the catheter under sterile conditions. According to some embodiments the plasma chamber is located within the surgery room or otherwise in a sterile field thus ensuring the sterile conditions of the plasma treatment. It should further be understood that the power source that provides the plasma generating EM power to the electrodes need not necessarily be near the plasma chamber or in the sterile field and may be located in another room and/or may be activated and operated under non-sterile conditions.

It is noted that, in the "closed system" approach and also in the "open system" approach, a second session of plasma treatment may be performed immediately after a first session, to improve or enhance the surface modification. According to some embodiments the second session is performed after a slight displacement of the internal electrode and/or the external electrode relative to the catheter, thereby minimizing the area that is effectively shaded by the spacer nets of the electrodes, and thereby practically reaching a full coverage of the plasma treatment over the nominally treated surfaces.

Following the plasma treatment as described above the catheter may be immediately employed in the medical procedure, namely deployed in the subject's body. According to some embodiments, the catheter may additionally or alternatively be exposed to a liquid, gel or powder prior to being taken to the medical procedure. According to some such embodiments, the plasma treatment facilitates and enhances adhesion of materials to the plasma-treated surfaces, and particularly enhances wettability, thus improving coverage of the treated surfaces by the material the catheter is exposed to. According to some embodiments the catheter may be exposed to a liquid containing a therapeutic agent, e.g. an antibiotic solution. According to some embodiments the plasma treatment renders the treated surfaces highly or perfectly wettable, thus leading to wetting of the treated surfaces by a polar liquid. Thus, exposing a catheter having surfaces treated with plasma according to the teachings herein to such solution may provide for the medical procedure a catheter being wet—namely fully covered—with an antibiotics solution.

According to some embodiments the catheter may be immersed and maintained in an aqueous solution such as saline after the plasma treatment and prior to the medical procedure, to preserve the surface modifications generated by the plasma treatment for a longer duration. According to some embodiments, such storing of the treated catheter immersed in a suitable solution may satisfactorily preserve the generated surface modifications for several days.

There is therefore provided according to an aspect of the invention a method for preparing a catheter (10), the catheter having an extraluminal surface (34) and an intraluminal surface (32), the intraluminal surface defining an elongated internal lumen (30) of the catheter, prior to an installation procedure in a live subject. The method comprises generating plasma adjacently to the intraluminal and extraluminal surfaces. Plasma generation is carried out by providing EM power to at least one internal electrode (100) inside the internal lumen of the catheter, and at least one external electrode (120) outside the internal lumen wherein the electrodes are detachable from the catheter and wherein the catheter is situated in a plasma chamber. The method further comprises removing the catheter from the plasma chamber under sterile conditions, and detaching the electrodes from the catheter. The method thereby provides the catheter having hydrophilic intraluminal and extraluminal surfaces.

According to some embodiments the EM power is at radio frequency (RF).

According to some embodiments the catheter is provided sterile, and the method further comprises, prior to the generating step, placing the catheter in the sterile plasma chamber under sterile conditions. The method further comprises positioning the at least one internal electrode inside the internal lumen of the catheter, and the at least one external electrode outside the internal lumen.

According to some embodiments the catheter is provided inside the plasma chamber, the plasma chamber being sealed and containing an ionizable fluid having a pre-defined composition and the catheter being immersed in the fluid. The internal electrode is inside the internal lumen of the catheter and the catheter is inside the external electrode. The method comprises generating plasma inside the plasma chamber without opening the sealed plasma chamber and without interfering with the composition of the ionizable fluid there inside.

According to some embodiments the method further comprise, following the step of generating plasma, wetting the catheter or a portion thereof with a polar liquid. According to some embodiments the polar liquid is an aqueous solution, aqueous suspension or blood. According to some embodiments the polar liquid includes a therapeutically effective agent, thereby coating the wetted portion of the catheter by the therapeutically effective agent.

According to some embodiments the method is carried out no more than 6 hours prior to the installation of the catheter in the subject. According to some embodiments of the method, plasma is generated for no longer than about 5 minutes.

According to some embodiments the, following removing the catheter from the plasma chamber the intraluminal and extraluminal surfaces have a surface tension of at least $$72 \cdot 10^{-3} \frac{N}{m}$$

at least along a portion thereof.

There is further provided according to an aspect of the invention a device for plasma treatment of a catheter (10), the catheter having an extraluminal surface (34) and an intraluminal surface (32), and the intraluminal surface defining an elongated internal lumen (30) of the catheter. The device comprises an internal electrode (100) comprising an elongated conductor (110) and a spacer net (112) made from a dielectric material enveloping the elongated conductor. The internal electrode is dimensioned and configured to enter into the internal lumen of the catheter. The device further comprises an external electrode (120) comprising a conductor sleeve (130) enveloping an external spacer net (132) made from a dielectric material and shaped as a sock. The external electrode is dimensioned and configured to allow insertion of the catheter into the external spacer net. The device further comprises a RF EM power source 162 configured to electrically associate with the internal electrode and with the external electrode, and to provide the electrodes with EM power sufficient to generate plasma adjacently to the extraluminal surface and the intraluminal surface when the catheter is inside the external electrode and the internal electrode is inside the lumen of the catheter. According to some embodiments the EM power is at radio frequency (RF).

According to some embodiments the elongated conductor of the internal electrode has a length of at least 20 cm. According to some embodiments the elongated conductor has a diameter of 1.0 mm or less. According to some embodiments the spacer net (112, 132) has a thickness of 0.1 mm or more and holes smaller than 10 mm across. According to some embodiments the elongated conductor of the internal electrode is flexible.

According to some embodiments the device further comprises a sealable plasma chamber (200), the plasma chamber including the internal electrode and external electrode there inside, and the EM power source is outside the plasma chamber.

According to some embodiments the plasma chamber further comprises a gas port (220) configured to allow pumping the plasma chamber and/or flushing the plasma chamber with a gas.

There is further provided according to an aspect of the invention a package for storing a catheter (10) under sterile conditions, the catheter having an extraluminal surface (34) and an internal lumen (30) defined by an intraluminal surface (32) of the catheter. The package contains a sealed encasing (200), containing an ionizable fluid having a pre-defined composition and configured to function as a plasma chamber. The package further contains the catheter sealed inside the sealed encasing, being immersed in the fluid. The package further contains an internal electrode (100) comprising an elongated conductor and a spacer net made from a dielectric material in a form of a net enveloping the internal conductor, the internal electrode being inside the internal lumen of the catheter. And the package further contains an external electrode (120) comprising a conductor sleeve enveloping an external spacer net made from a dielectric material, wherein the catheter is inside the external electrode. The package is configured for generating plasma adjacent to the extraluminal and the intraluminal surfaces of the catheter inside the sealed encasing, by individually electrically associating the internal electrode and the external electrode to a RF EM power source positioned outside the sealed encasing, without opening the sealed plasma chamber and without interfering with the composition of the ionizable fluid there inside.

It is appreciated that certain features of the invention which are described in the context of separate embodiments, may also be provided in combination in a single embodiment. Conversely, various features of the invention, which are described in the context of a single embodiment, may also be provided separately or in any suitable sub-combination or as suitable in any other described embodiment of the invention. No feature described in the context of an embodiment is to be considered an essential feature of that embodiment, unless explicitly specified as such.

Although steps of methods according to some embodiments may be described in a specific sequence, methods of the invention may comprise some or all of the described steps carried out in a different order. A method of the invention may comprise all of the steps described or only a few of the described steps. No particular step in a disclosed method is to be considered an essential step of that method, unless explicitly specified as such.

Although the invention is described in conjunction with specific embodiments thereof, it is evident that numerous alternatives, modifications and variations that are apparent to those skilled in the art may exist. Accordingly, the invention embraces all such alternatives, modifications and variations that fall within the scope of the appended claims. It is to be understood that the invention is not necessarily limited in its application to the details of construction and the arrangement of the components and/or methods set forth herein. Other embodiments may be practiced, and an embodiment may be carried out in various ways.

The phraseology and terminology employed herein are for descriptive purpose and should not be regarded as limiting. Citation or identification of any reference in this application shall not be construed as an admission that such reference is available as prior art to the invention. Section headings are used herein to ease understanding of the specification and should not be construed as necessarily limiting.

The invention claimed is:

1. A method for preparing a catheter for an installation procedure in a live subject by increasing a catheter's surface's wettability, the method comprising:
providing the catheter, wherein the catheter has an extraluminal surface and an intraluminal surface, the intraluminal surface defining an elongated internal lumen of the catheter;
generating plasma adjacent to at least a portion of the intraluminal and extraluminal surfaces, by providing electromagnetic (EM) power to at least one internal electrode inside the elongated internal lumen of the catheter, wherein the electrode is detachable from the catheter; and
detaching the at least one internal electrode from the catheter, thereby providing the catheter with hydrophilic intraluminal and extraluminal surfaces along at least a portion thereof.

2. The method of claim 1, further comprising placing the catheter in a sterile plasma chamber prior to the act of generating the plasma.

3. The method of claim 2, further comprising pumping gas from the plasma chamber and/or flowing gas into the plasma chamber.

4. The method of claim 1, further comprising positioning at least one external electrode outside the elongated internal lumen, wherein the plasma is generated in the act of generating the plasma by a plasma-generating EM field between the internal electrode and the external electrode.

5. The method of claim 1 wherein:
the catheter is provided inside a plasma chamber;
the plasma chamber is sealed and contains an ionizable fluid having a pre-defined composition; and the catheter is immersed in the fluid, the internal electrode being inside the elongated internal lumen of the catheter.

6. The method of claim 1 further comprising, following the act of generating the plasma, wetting the catheter or a portion thereof with a polar liquid.

7. The method of claim 6 wherein the polar liquid includes an aqueous solution, aqueous suspension, or blood.

8. The method of claim 6 wherein the polar liquid includes a therapeutically effective agent.

9. The method of claim 6, further comprising, following the act of wetting, maintaining the catheter immersed in the polar liquid to preserve high surface hydrophilicity.

10. The method of claim 1 being carried out no more than 6 hours prior to the installation of the catheter in the subject.

11. The method of claim 1 wherein the plasma is generated for no longer than about 5 minutes.

12. The method of claim 1 wherein, following the act of detaching of the internal electrode from the catheter, the hydrophilic intraluminal or extraluminal surfaces have a surface tension of at least $$72 \cdot 10^{-3} \frac{N}{m}.$$

* * * * *